US00PP29086P2

(12) United States Plant Patent
Kamstra

(10) Patent No.: US PP29,086 P2
(45) Date of Patent: Mar. 6, 2018

(54) ***SOLIDAGO* PLANT NAMED 'BARSOLMAG'**

(50) Latin Name: *Solidago hybrida*
Varietal Denomination: BARSOLMAG

(71) Applicant: BARTELS STEK B.V., Aalsmeer (NL)

(72) Inventor: Silvan Kamstra, Kudelstaart (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,639

(22) Filed: Oct. 22, 2016

(51) Int. Cl.
*A01H 5/02* (2006.01)

(52) U.S. Cl.
USPC ..... Plt./483

(58) Field of Classification Search
USPC ..... Plt./483
See application file for complete search history.

*Primary Examiner* — Annette H Para
(74) *Attorney, Agent, or Firm* — C. A. Whealy

(57) ABSTRACT

A new and distinct cultivar of *Solidago* plant named 'BARSOLMAG', characterized by its upright plant habit; freely branching growth habit; early and freely flowering habit; unique flat-top spray formation; and inflorescences with light yellow-colored ray florets.

2 Drawing Sheets

Botanical designation: *Solidago hybrida.*
Cultivar denomination: 'BARSOLMAG'.

BACKGROUND OF THE INVENTION

The present invention relates to a new and distinct *Solidago* plant, botanically known as *Solidago hybrida*, and hereinafter referred to by the name 'BARSOLMAG'.

The new *Solidago* plant is a product of a planned breeding program conducted by the Inventor in Aalsmeer, The Netherlands. The objective of the program is to create and develop new *Solidago* plants with attractive inflorescences.

The new *Solidago* originated from a cross-pollination made by the Inventor on Jun. 1, 2009 of a proprietary selection of *Solidago hybrida* identified as code number SO-0007, not patented, as the female, or seed, parent with a proprietary selection of *Solidago hybrida* identified as code number SO08-000042-020, not patented, as the male, or pollen, parent. The new *Solidago* plant was discovered and selected by the Inventor as a single flowering plant within the progeny of the stated cross-pollination in a controlled environment in Aalsmeer, The Netherlands on Jun. 1, 2010.

Asexual reproduction of the new *Solidago* plant by vegetative terminal cuttings in a controlled environment in Aalsmeer, The Netherlands since Jan. 1, 2012, has shown that the unique features of this new *Solidago* plant are stable and reproduced true to type in successive generations.

SUMMARY OF THE INVENTION

Plants of the new *Solidago* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BARSOLMAG'. These characteristics in combination distinguish 'BARSOLMAG' as a new and distinct *Solidago* plant:

1. Upright plant habit.
2. Freely branching growth habit.
3. Early and freely flowering habit.
4. Unique flat-top spray formation.
5. Inflorescences with light yellow-colored ray florets.

Plants of the new *Solidago* differ from plants of the female parent selection in the following characteristics:

1. Sprays of plants of the new *Solidago* are flat-top in shape whereas sprays of plants of the female parent selection are plume-shaped.
2. Inflorescences of plants of the new *Solidago* are slightly larger than inflorescences of plants of the female parent selection.

Plants of the new *Solidago* differ from plants of the male parent selection in the following characteristics:

1. Plants of the new *Solidago* are taller than plants of the male parent selection.
2. Sprays of plants of the new *Solidago* are flatter in shape than sprays of plants of the male parent selection.

Plants of the new *Solidago* can be compared to plants of *Solidago hybrida* 'Bareight', disclosed in U.S. Plant Pat. No. 12,525. In side-by-side comparisons, plants of the new *Solidago* differ from plants of 'Bareight' in the following characteristics:

1. Plants of the new *Solidago* have longer and thicker lateral branches than plants of 'Bareight'.
2. Inflorescences of plants of the new *Solidago* have more ray and disc florets than inflorescences of plants of 'Bareight'.
3. Sprays of plants of the new *Solidago* are flat-top in shape whereas sprays of plants of 'Bareight' are plume-shaped.
4. Inflorescences of plants of the new *Solidago* are larger than inflorescences of plants of 'Bareight'.

Plants of the new *Solidago* can also be compared to plants of *Solidago hybrida* 'Golden Glory', not patented. In side-by-side comparisons, plants of the new *Solidago* differ from plants of 'Golden Glory' in the following characteristics:

1. Plants of the new *Solidago* are shorter than plants of 'Golden Glory'.

2. Sprays of plants of the new *Solidago* are flat-top in shape whereas sprays of plants of 'Golden Glory' are plume-shaped.
3. Inflorescences of plants of the new *Solidago* are larger than inflorescences of plants of 'Golden Glory'.

BRIEF DESCRIPTION OF THE PHOTOGRAPHS

The accompanying photographs illustrate the overall appearance of the new *Solidago* plants. These photographs shows the colors as true as it is reasonably possible to obtain in colored reproductions of this type. Colors in the photographs may differ slightly from the color values cited in the detailed botanical description which accurately describe the colors of the new *Solidago* plant.

The photograph on the first sheet comprises a side perspective view of a typical flowering stem of 'BARSOLMAG'.

The photograph on the second sheet is a close-up view of a typical flowering spray of 'BARSOLMAG'.

DETAILED BOTANICAL DESCRIPTION

In the following description, color references are made to The Royal Horticultural Society Colour Chart, 2005 Edition, except where general terms of ordinary dictionary significance are used. The aforementioned photographs, following observations and measurements describe plants grown in Naivasha, Kenya during the winter in ground beds in an outdoor nursery and under cultural practices which approximate those generally used in commercial *Solidago* production. During the production of the plants, day temperatures averaged 20° C. and night temperatures averaged 10° C. Measurements and numerical values represent averages for typical flowering plants. Plants were pinched one time and were about six months old when the photographs and description were taken.

Botanical classification: *Solidago hybrida* 'BARSOLMAG'.

Parentage:

*Female, or seed, parent.*—Proprietary selection of *Solidago hybrida* identified as code number SO-0007, not patented.

*Male, or pollen, parent.*—Proprietary selection of *Solidago hybrida* identified as code number SO08-000042-020, not patented.

Propagation:

*Type.*—Terminal vegetative cuttings.

*Time to initiate roots, summer.*—About seven days at temperatures about 20° C.

*Time to initiate roots, winter.*—About nine days at temperatures about 20° C.

*Time to produce a rooted young plant, summer.*—About four to five weeks at temperatures about 20° C.

*Time to produce a rooted young plant, winter.*—About five weeks at temperatures about 18° C.

*Root description.*—Fine, fibrous; white in color.

*Rooting habit.*—Moderately freely branching; dense.

Plant description:

*Plant and growth habit.*—Perennial plant typically grown as a cut flower in ground beds; upright and bushy plant habit; vigorous growth habit and rapid growth rate.

*Plant height, soil level to top of foliar plane.*—About 40 cm to 50 cm.

*Plant height, soil level to top of floral plane.*—About 60 cm to 70 cm.

*Plant diameter.*—About 30 cm to 40 cm.

*Productivity.*—Highly productive, plants produce about 25 flowering stems per year.

*Lateral branches.*—Internode length: About 3 cm to 4 cm. Strength: Strong. Texture and luster: Pubescent, minute; semi-glossy. Color: Close to 137C.

*Leaves.*—Arrangement: Alternate, simple; sessile. Length: About 15 cm to 20 cm. Width; About 3 cm. Shape: Lanceolate. Apex: Acute. Base: Acute. Margin: Entire to serrate. Texture and luster, upper and lower surfaces: Smooth, glabrous; matte. Venation pattern: Parallel. Color: Developing and fully expanded leaves, upper surface: Close to 137B; venation, close to 137B. Developing and fully expanded leaves, lower surface: Close to 137C; venation, close to 137C.

Inflorescence description:

*Inflorescence form and flowering habit.*—Single-type inflorescence form with obcordate to lanceolate-shaped ray florets; flowering sprays are flat-top in shape; freely flowering habit with about 500 inflorescences developing per plant; disc and ray florets develop acropetally on a capitulum; inflorescences face mostly upright; uniform flowering habit.

*Fragrance.*—None detected.

*Inflorescence longevity.*—Inflorescences maintain good substance for about three weeks on the plant and for about two weeks as a cut flower; inflorescences persistent.

*Flowering response.*—Plants flower naturally during the autumn; early flowering habit, plants begin flowering about six weeks after pinching.

*Inflorescence buds.*—Height: About 5 mm. Diameter: About 4 mm. Shape: Oval. Texture and luster: Smooth, glabrous; matte. Color: Close to 151D.

*Spray height.*—About 30 cm.

*Spray diameter.*—About 15 cm.

*Inflorescence size.*—Diameter: About 1.1 cm. Depth (height): About 5 mm. Diameter of disc: About 3 mm. Receptacle height: About 2 mm. Receptacle diameter: About 1 mm. Receptacle color: Close to 137C.

*Ray florets.*—Quantity and arrangement: About 20 arranged in a single whorl; mostly horizontal. Length: About 4 mm. Width: About 0.5 mm. Shape: Obcordate to lanceolate. Apex: Obtuse. Base: Attenuate. Margin: Entire. Texture and luster, upper and lower surfaces: Smooth, glabrous; matte. Color: When opening, upper and lower surfaces: Close to 4A. Fully opened, upper and lower surfaces: Close to 4A.

*Disc florets.*—Quantity and arrangement: About 25, massed at center of receptacle. Length: About 1 mm. Diameter: About 0.5 mm. Shape: Tubular. Apex: Rounded. Texture and luster: Smooth, glabrous; matte. Color, immature and mature: Close to 4A.

*Peduncles.*—Length, terminal peduncle: About 20 cm. Diameter, terminal peduncle: About 4 mm. Length, third peduncle: About 5 mm. Diameter, third peduncle: About 2 mm. Aspect, terminal peduncle: Mostly upright. Aspect, third peduncle: About 20° from vertical. Strength: Strong. Texture and luster: Smooth, glabrous; matte. Color: Close to 137C.

*Reproductive organs*.—Androecium: Present on disc florets only. Quantity per disc floret: One. Anther shape: Elliptic. Anther length: Less than 1 mm. Anther color: Close to 14A. Pollen amount: None observed. Gynoecium: Present on both ray and disc florets. Quantity per floret: One. Stigma shape: Filamentous. Stigma color: Close to 155A. Style length: Less than 1 mm. Style color: Close to 155A.

*Seed*.—Seed development has not been observed on plants of the new *Solidago*.

Pathogen & pest resistance: Plants of the new *Solidago* have not been observed to be resistant to pathogens and pests common to *Solidago* plants.

Temperature tolerance: Plants of the new *Solidago* have been observed to tolerate temperatures ranging from about −15° C. to about 30° C.

It is claimed:

1. A new and distinct *Solidago* plant named 'BARSOL-MAG' as illustrated and described.

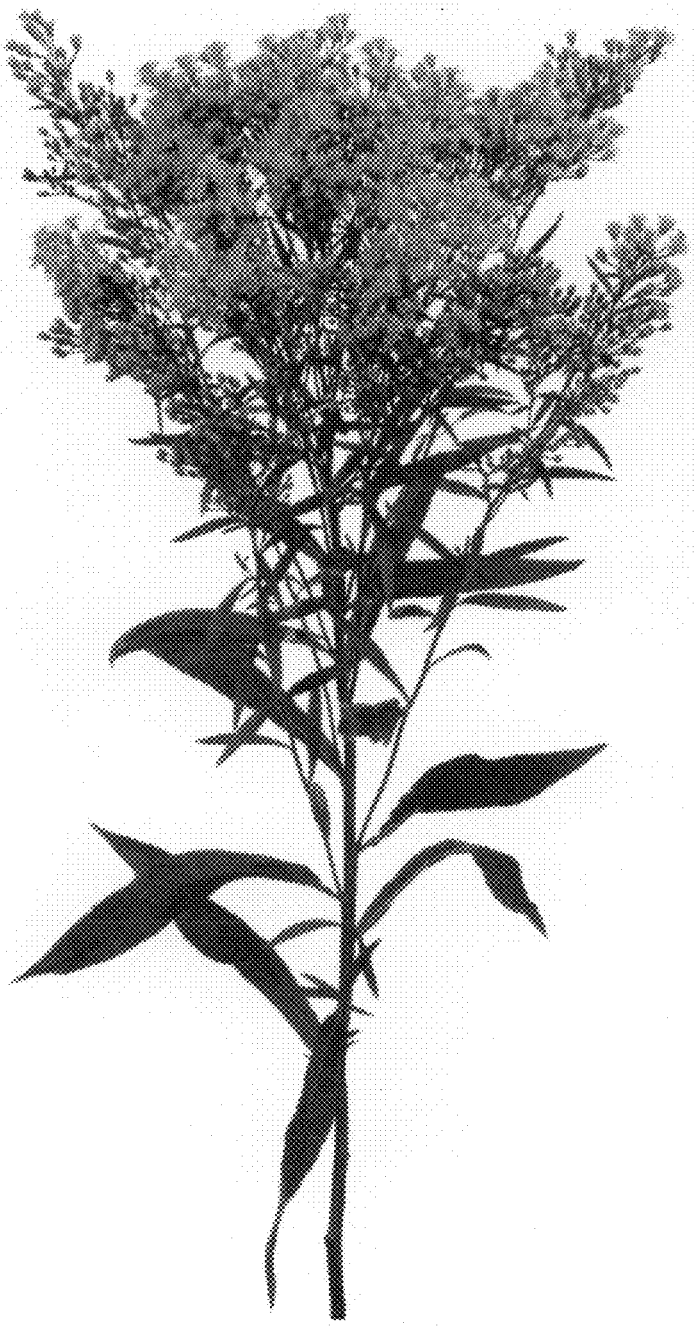

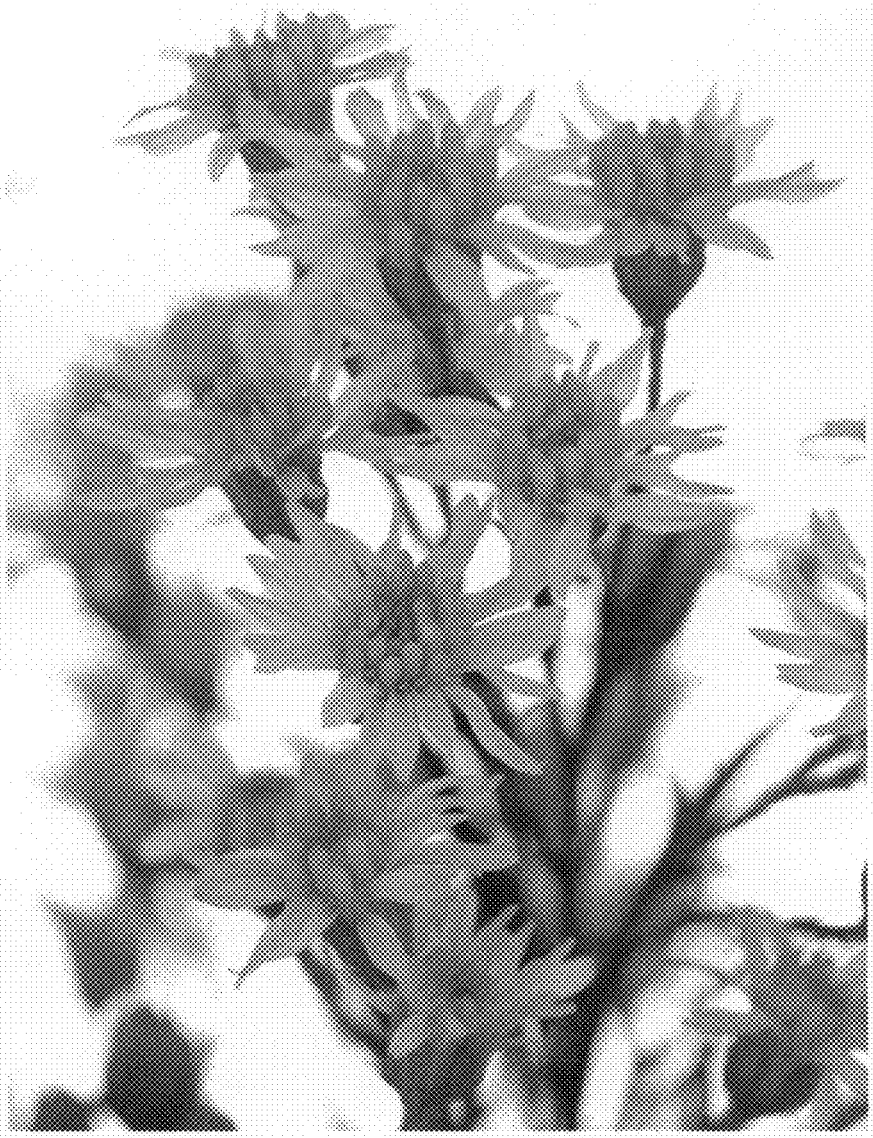

* * * * *